(12) United States Patent
Pudleiner et al.

(10) Patent No.: US 7,705,073 B2
(45) Date of Patent: *Apr. 27, 2010

(54) PROCESS FOR PREPARATION OF ANTIMICROBIAL PLASTICS COMPOSITIONS

(75) Inventors: Heinz Pudleiner, Krefeld (DE); Joachim Hyner, Langenfeld (DE)

(73) Assignee: Bayer Innovation GmbH, Dusseldorf (DE)

( * ) Notice: Subject to any disclaimer, the term of this patent is extended or adjusted under 35 U.S.C. 154(b) by 269 days.

This patent is subject to a terminal disclaimer.

(21) Appl. No.: 11/539,263

(22) Filed: Oct. 6, 2006

(65) Prior Publication Data

US 2008/0071229 A1    Mar. 20, 2008

(30) Foreign Application Priority Data

Oct. 6, 2005    (DE) .................. 10 2005 048 132

(51) Int. Cl.
*C08K 5/34* (2006.01)
*C09D 5/16* (2006.01)
*C08G 18/28* (2006.01)
*A61K 9/22* (2006.01)

(52) U.S. Cl. .............. 524/99; 523/122; 524/590; 604/890.1

(58) Field of Classification Search .......... 424/422, 424/423, 426; 523/122; 524/590, 99; 604/890.1
See application file for complete search history.

(56) References Cited

U.S. PATENT DOCUMENTS

| 6,224,579 | B1 * | 5/2001 | Modak et al. ............ 604/265 |
| 6,455,059 | B1 * | 9/2002 | Albers et al. ............ 424/405 |
| 6,475,631 | B1 * | 11/2002 | Yamamoto et al. ........ 428/480 |
| 6,527,995 | B1 * | 3/2003 | Kaufhold et al. .......... 264/126 |
| 6,605,069 | B1 * | 8/2003 | Albers et al. ............ 604/264 |
| 6,723,333 | B1 * | 4/2004 | Albers et al. ............ 424/422 |

OTHER PUBLICATIONS

STN Search Report, pp. 1-2.*

* cited by examiner

*Primary Examiner*—Vasu Jagannathan
*Assistant Examiner*—Alexander C Kollias
(74) *Attorney, Agent, or Firm*—Baker Donelson Bearman, Caldwell & Berkowitz, PC

(57) ABSTRACT

The present invention relates to a process for preparing antimicrobial plastics compositions comprising a thermoplastic, particularly of thermoplastic elastomer, and at least one pulverulent antimicrobial active ingredient, specifically from the group of the bis(4-amino-1-pyridinium)alkanes, and to the use of this plastics composition for catheters and other medical-technology products.

25 Claims, 1 Drawing Sheet

PROCESS FOR PREPARATION OF ANTIMICROBIAL PLASTICS COMPOSITIONS

CROSS REFERENCE TO A RELATED APPLICATION

This application claims priority to German Application No. 102005048132.9 filed Oct. 6, 2005, the content of which is incorporated herein by reference in its entirety.

BACKGROUND OF THE INVENTION

1. Field of the Invention

The present invention relates generally to a process for preparation of antimicrobial plastics compositions comprising a thermoplastic, particularly of thermoplastic elastomer, and of at least one pulverulent antimicrobial active ingredient, specifically from the group of the bis(4-amino-1-pyridinium) alkanes, and to the use of this plastics composition for catheters and other medical-technology products.

2. Description of Related Art

Numerous studies have shown that coagulase-negative staphylococci, the transient microbe Staphylococcus aureus, Staphylococcus epidermis and various Candida species have heretofore been the main causes of catheter-associated infections. During application of the catheter, these microorganisms, which are ubiquitously present on the skin, penetrate the physiological barrier of the skin and thus reach the subcutaneous region and eventually the bloodstream. Adhesion of the bacteria to the plastics surface is regarded as an essential step in the pathenogenesis of foreign-body infections. Adhesion of the cutaneous organisms to the polymer surface is followed by the start of metabolically active proliferation of the bacteria with colonization of the polymer. This is associated with production of a biofilm through bacterial excretion of extracellular glycocalix.

Pre-, peri- or post-operative measures (e.g. hygiene measures, etc.) are only a partial solution to these problems. A rational strategy for prevention of polymer-associated infections involves a modification of the polymeric materials used. The aim of such a modification generally involves inhibition of the adhesion of bacteria and, respectively, of proliferation of existing adherent bacteria, for causal prevention of foreign-body infections. By way of example, this can be achieved by incorporating a suitable chemotherapeutic agent into the polymer matrix (e.g. antibiotics and antiseptics), provided that the incorporated active ingredient can also diffuse out of the polymer matrix. In this case, it is possible to extend the release of the antimicrobial active ingredient over a prolonged period, and thus the processes of adhesion of microbes or, more precisely, adhesion of bacteria and, respectively, their proliferation on the polymer can correspondingly be inhibited for a prolonged period.

There are previously known methods for preparing antimicrobially modified polymers. The microbicides in such processes are applied onto the surface or onto a surface layer or introduced into the polymeric material. The following techniques have been described for thermoplastic polyurethanes, which are particularly used for medical applications:

a) adsorption on the polymer surface (passively or via surfactants)
b) introduction into a polymer coating which is applied on the surface of a molding
c) incorporation into the bulk phase of the polymeric substrate material
d) covalent bonding to the polymer surface
e) mixing with a polyurethane-forming component prior to the reaction to give the finished polymer.

The prior art examined below concerns incorporation of active ingredients into the bulk phase of the polymeric substrate material.

U.S. Pat. No. 5,281,677 describes blends composed of TPU which are preferably used for production of multiple-lumen vascular catheters. It is said that the moldings can also comprise an antimicrobial active ingredient, which can have been bulk-distributed in one of the polyurethanes prior to processing in the melt.

U.S. Pat. No. 6,120,790 describes thermoplastic resins which comprise antimicrobial or fungistatic active ingredients, where the polymer contains a polyether chain as unit. Active ingredients that could be used would include pyridines, among organic compounds, but these are not specified as examples.

EP 927 222 B1 describes the introduction of antithrombically or antibiotically active substances into the reaction mixture for preparation of a TPU.

U.S. Pat. No. 5,906,825 describes polymers, among which are polyurethanes, in which biocides and, respectively, antimicrobial agents (specific description being exclusively of plant ingredients) have been dispersed, the amount being sufficient to suppress the growth of microorganisms coming into contact with the polymer. This can be optimized via addition of an agent which regulates the migration and/or release of the biocide. Naturally occurring substances such as vitamin E are mentioned. Food packaging is the main application.

JP 08-157641 describes a process for preparation of antimicrobial materials via kneading, in the melt, of a polymer, among which is polyurethane, the specific surface area of the polymer being greater than or equal to 17 $cm^2/g$, with a pulverulent active ingredient, preferably chlorhexidine.

CN 1528470 A describes a process for production of a medical anti-infection insertion guide tube for catheters composed of polyurethane, where a masterbatch termed a mother material, which comprises the antimicrobial agent, is mixed with the PU raw material and is extruded to give the molding.

A feature common to all of the processes mentioned supra is that at least one antimicrobial active ingredient is incorporated into the melt of the polymeric substrate material, and the time-limited long-term action of the antimicrobial modification of the moldings made of polymeric material, (in particular of medical products during use on or in a patient) is optimized. However, there is no satisfactorily secure and simultaneous provision in the prior art of such features together with an ability to minimize the risk of initial microbial infection of the molding itself or microbial infection of humans and animals via the molding.

The medical products discussed above are mainly used intracorporally. By way of example and as described supra, catheters penetrate the surface of the body for the entire period of their use and therefore pose particularly high risk of microbial infection. The risk of initial infection via introduction of medical products into the body due to microbial contamination has not yet been sufficiently reduced via the known methods of antimicrobial modification.

Conventional active ingredients generally are in the form of fine powders. Only very small amounts of the active ingredients are typically needed in the plastic for the desired action on the plastics surface. A requirement has therefore been precise metering of small amounts of the antimicrobially active substances coupled with the presence of these substances in fine dispersion at identical concentration in every region of the medical product.

SUMMARY OF THE INVENTION

It was an object of the invention to provide a process for production of antimicrobially modified plastics which are intended in particular for medical items, such as catheters, and which have at least one antimicrobial active ingredient present in very fine dispersion, and which efficiently inhibit surface colonization via microbes over a prolonged period (preferably at least 4 weeks or more), and which release the active ingredient continuously over a 15-day period.

It has now been found that this object can be achieved if, instead of the conventional metering of the pure active ingredient in the form of powder into a melt of the plastic, a mixture of the active ingredient together with the plastics powder is used.

Additional objects, features and advantages of the invention will be set forth in the description which follows, and in part, will be obvious from the description, or may be learned by practice of the invention. The objects, features and advantages of the invention may be realized and obtained by means of the instrumentalities and combination particularly pointed out in the appended claims.

BRIEF DESCRIPTION OF THE DRAWINGS

The accompanying drawings, which are incorporated in and constitute a part of the specification, illustrate a presently preferred embodiment of the invention, and, together with the general description given above and the detailed description of the preferred embodiment given below, serve to explain the principles of the invention.

DETAILED DESCRIPTION OF A PREFERRED EMBODIMENT

Figure 1:
FIG. 1 is an SEM micrograph of a comparative example.

The instant process ensures that the moldings have a concentration which suppresses colonization by microbes at the plastics surface, over a prolonged period.

Plastics compositions of the present invention are preferably antimicrobial, that is, the concentration of the active ingredient is preferably sufficient to suppress, at least significantly to reduce, over a prolonged period, colonization by undesired microbes. This period is preferably at least 2 weeks, particularly preferably more than 4 weeks. Undesired microbes means any bacteria, viruses and fungi, as well as other microbes known to one of skill in the art.

The present invention further provides preparation of the inventive plastics composition. The inventive plastics compositions are preferably prepared via thermoplastic processing and further processed.

Any active ingredient can be used. In principle, the following active ingredients are suitable as long as they have antimicrobial properties: ansamycin derivatives (rifamycin, rifapentin), and mention is preferably made of antimicrobial substances which have also been used for clinical purposes for what are known as difficult-to-treat infections. In principle, it is possible to use any antimicrobially active group, e.g. lipophilic members of the aminoglycosides group, of the cephalosporins group and beta-lactams based thereon, of chloramphenicol, lincosamides, macrolides, penicillins, quinolones, sulphonamides, tetracyclins, except the combination tetracyclin-minocyclin. Lipophilic antibiotics are preferably benzathin, phenoxymethylpenicillin, chloramphenicol, chlortetracyclin, ciprofloxacin betaine, ciprofloxacin, clarithromycin, clindamycin palmitate hydrochloride, trimethoprim, erythromycin 2-acetate, and the corresponding stearate; erythromycin estolate, erythromycin ethylsuccinate, erythromycin glutamate, erythromycin lactopropionate, erythromycin stearate, fusidinic acid, preferably free fusidinic acid, gramicidin, mupirocin, lipophilic members of the imidazole series, such as econazole, itraconazole, clotrimazole and others, pristinamycin, rifabutin, rifapentin, rifampicin, silver sulfadiazine.

Particularly preferred active ingredients that can be used are in principle any of the active ingredients defined in Patent claims 1 to 4 on p. 28 of DE 27 08 331 C2 incorporated herein by reference. It is preferable to use the compounds from Examples 1-82 (p. 5 to p. 18, line 19) incorporated herein by reference, and it is particularly preferable to use octenidine or its hydrochloride, or very particularly preferably the dihydrochloride 1,1'-(1,10-decanediyl)bis[4-(octylamino)pyridinium] dichloride.

These active ingredients termed bis(4-(substituted amino)-1-pyridinium)alkanes are defined via the formulae (I) and (II)

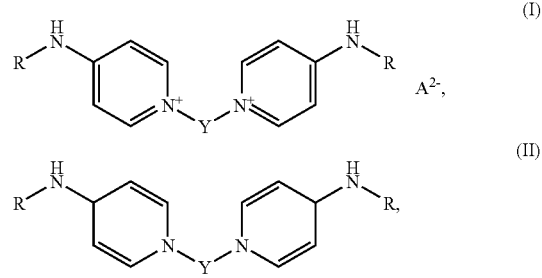

wherein
Y is an alkylene group having from 4 to 18 carbon atoms,
R is $C_6$-$C_{18}$-alkyl, $C_5$-$C_7$-cycloalkyl or halogen-atom-substituted phenyl and
A is two monovalent anions or one divalent anion.
Y is preferably 1,10-decylene or 1,12-dodecylene, particularly preferably 1,12-dodecylene.
R is preferably n-hexyl, n-heptyl or n-octyl, particularly preferably n-octyl.
A is by way of example a sulphate or in each case 2 fluoride, chloride, bromide, iodide, or methanesulphonate ions, preferably in each case 2 fluoride, chloride, or bromide ions, particularly preferably 2 chloride ions.

The radicals of formula I and II can independently be the same or different in each instance. Formula (II) indicates the corresponding free bases which can be prepared via neutralization from the salts of the formula (I) by the conventional methods of organic chemistry. The salts of the formula (I) are also often seen in the literature in the form of the formula (III)

formula (II)×$H_2A$ (III), where "formula (II)" and A are defined as stated above. A chemical formula is naturally only a simplified representation of reality. In this case there are tautomers for which there is no indication that they are distinguishable under commonly encountered conditions and temperatures. Nevertheless, for octenidine dihydrochloride there are 2 Chemical Abstracts Registry numbers and 2 numbers in the European list of approved substances all of which are incorporated herein by reference. For the present invention it is to be of no relevance whether compounds of the formula (I) or of the formula (III) are used, or which form these take in the polymer composition. It may be preferable to use salts of the formula (I) or (III) in some cases.

The median particle size $d_{50}$ of the active ingredient is preferably from about 0.5 to about 20 μm, particularly preferably from about 1 to about 10 μm.

Suitable plastics include in principle any thermoplastic, as long as its processing temperature does not deactivate the active ingredient used, but particularly thermoplastic elastomers (TPE). TPEs are materials that comprise elastomeric phases physically incorporated therein by mixing the elastomeric phase into thermoplastically processible polymers or by incorporating them into the polymers by chemical bonding. A distinction is made between polymer blends, in which the elastomeric phases present have been incorporated by physical mixing, and block copolymers, in which the elastomeric phases are a constituent per se of the polymeric structure. By virtue of the structure of the thermoplastic elastomers, there are hard and soft regions present alongside one another. The hard regions form a crystalline network structure or a continuous phase whose interstices have been filled by elastomeric segments. By virtue of this structure, these materials have rubber-like properties.

3 main groups of thermoplastic elastomers can preferably be used:
1. copolyesters
2. polyether block amides (PEBA)
3. thermoplastic polyurethanes (TPU)

DE-A 22 39 271, DE-A 22 13 128, DE-A 24 49 343 and U.S. Pat. No. 3,023,192 all incorporated herein by reference each disclose a process for synthesis of copolyesters of this type. For the purposes of the present invention, examples of suitable copolyesters include those based on terephthalic acid with certain proportions of isophthalic acid, and/or butanediol and polyethers, preferably $C_4$ polyethers, based on tetrahydofuran and, by way of example, obtainable for example from Hytrel™ from Du Pont, Pelpren™ from Toyobo, Arnitel™ from Akzo or Ectel™ from Eastman Kodak.

French Patent 7 418 913 (publication No. 2 273 021), DE-A 28 02 989, DE-A 28 37 687, DE-A 25 23 991, EP 0 095 893 B2, DE-A 27 12 987 and DOS 27 16 004 all incorporated herein by reference each disclose a process for synthesis of the PEBA polymers. According to the present invention, particularly suitable PEBA polymers include those which unlike those described above, have a random structure. Examples of suitable units include adipic acid, aminododecanoic acid, a proportion of hexamethylenediamine, polytetrahydrofuran, and/or a proportion of polyethylene glycol.

The thermoplastically processible polyurethanes that can be used according to the invention are preferably obtainable via reaction of the following polyurethane-forming components:
A) organic diisocyanate,
B) linear hydroxy-terminated polyol whose number average Mn molecular weight is from about 500 to about 10 000,
C) chain extender whose molecular weight is from about 60 to about 500, where the molar ratio of the NCO groups in A) to the groups reactive towards isocyanate in B) and C) is preferably from about 0.9 to about 1.2.

Examples of suitable organic diisocyanates A) that can be used include aliphatic, cycloaliphatic, heterocyclic and aromatic diisocyanates, as described in Justus Liebigs Annalen der Chemie, 562, pp. 75-136 which is incorporated herein by reference. Aliphatic and cycloaliphatic diisocyanates are preferred in some instances.

Individual compounds which may be mentioned by way of example include: aliphatic diisocyanates, such as hexamethylene diisocyanate, cycloaliphatic diisocyanates, such as isophorone diisocyanate, cyclohexane 1,4-diisocyanate, 1-methylcyclohexane 2,4-diisocyanate and 1-methylcyclohexane 2,6-diisocyanate, and also the corresponding isomer mixtures, dicyclohexylmethane 4,4'-diisocyanate, dicyclohexylmethane 2,4'-diisocyanate and dicyclohexylmethane 2,2'-diisocyanate, and also the corresponding isomer mixtures, aromatic diisocyanates, such as tolylene 2,4-diisocyanate, mixtures composed of tolylene 2,4-diisocyanate and tolylene 2,6-diisocyanate, diphenylmethane 4,4'-diisocyanate, diphenylmethane 2,4'-diisocyanate and diphenylmethane 2,2'-diisocyanate, mixtures composed of diphenylmethane 2,4'-diisocyanate and diphenylmethane 4,4'-diisocyanate, urethane-modified liquid diphenylmethane 4,4'-diisocyanate and diphenylmethane 2,4'-diisocyanate, 4,4'-diisocyanato-(1,2)-diphenylethane and naphthylene 1,5-diisocyanate. It is preferable to use hexamethylene 1,6-diisocyanate, isophorone diisocyanate, dicyclohexylmethane diisocyanate, diphenylmethane diisocyanate isomer mixtures with >96% by weight content of diphenylmethane 4,4'-diisocyanate and in particular diphenylmethane 4,4'-diisocyanate and naphthylene 1,5-diisocyanate. The diisocyanates mentioned may be used individually or in the form of mixtures with one another. They can optionally also be used together with up to about 15% by weight (based on the total amount of diisocyanate) of a polyisocyanate, for example with triphenylmethane 4,4',4"-triisocyanate or with polyphenyl polymethylene polyisocyanates.

The component B) used comprises linear hydroxy-terminated polyols whose number average molecular weight Mn is preferably from about 500 to about 10 000, more preferably from about 500 to about 5000, particularly preferably from about 600 to about 2000. As a consequence of the production process, these polyols often comprise small amounts of branched compounds. A term often used is therefore "substantially linear polyols". Preference is given to polyetherdiols, polycarbonatediols, sterically hindered polyesterdiols, hydroxy-terminated polybutadienes, and mixtures of these.

Other soft segments that can be used if desired include polysiloxanediols of formula (IV)

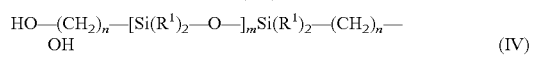

where
$R^1$ can independently be the same or different in each instance and is an alkyl group having from 1 to 6 carbon atoms or a phenyl group,
m is from 1 to 30, preferably from 10 to 25 and particularly preferably from 15 to 25, and
n can independently be the same or different in each instance and is from 3 to 6, which can be used alone or in a mixture with the abovementioned diols. These are known products and can be prepared by synthesis methods known per se, for example via reaction of a silane of formula (V)

where $R^1$ and m are as defined above, in a ratio of 1:2 with an unsaturated, aliphatic or cycloaliphatic alcohol, e.g. allyl alcohol, buten-(1)-ol or penten-(1)-ol in the presence of a catalyst, e.g. hexachloroplatinic acid.

Suitable polyetherdiols can be prepared for example by reacting one or more alkylene oxides preferably having from 2 to 4 carbon atoms in the alkylene radical with a starter molecule which contains two active hydrogen atoms. Examples of alkylene oxides that may be mentioned include: ethylene oxide, propylene 1,2-oxide, epichlorohydrin and butylene 1,2-oxide and butylene 2,3-oxide. It is preferable in some cases to use ethylene oxide, propylene oxide and/or mixtures comprising propylene 1,2-oxide and ethylene oxide. The alkylene oxides can be used individually, or in alternating succession, or in the form of mixtures. Examples of suitable starter molecules that can be used include: water, amino alcohols, such as N-alkyldiethanolamines, e.g. N-methyldiethanolamine, and diols, such as ethylene glycol, propylene 1,3-glycol, 1,4-butanediol and 1,6-hexanediol. Mixtures of starter molecules can also be used, if appropriate. Other suitable polyetherdiols include tetrahydrofuran polymerization products containing hydroxy groups. It is also possible to use proportions of from 0 to about 30% by weight, based on the bifunctional polyethers, of trifunctional polyethers, their amount being, however, preferably no more than that giving a thermoplastically processable product. The substantially linear polyetherdiols can be used either individually or else in the form of mixtures with one another.

Examples of suitable sterically hindered polyesterdiols can be prepared from dicarboxylic acids preferably having from 2 to 12 carbon atoms, particularly preferably from 4 to 6 carbon atoms, and from polyhydric alcohols. Examples of dicarboxylic acids that can be used include: aliphatic dicarboxylic acids, such as succinic acid, glutaric acid, adipic acid, suberic acid, azelaic acid and sebacic acid and aromatic dicarboxylic acids, such as phthalic acid, isophthalic acid and terephthalic acid. The dicarboxylic acids can be used individually or in the form of mixtures, e.g. in the form of a mixture of succinic, glutaric and adipic acid. To prepare the polyester diols it can, if appropriate, be advantageous to use, instead of the dicarboxylic acids, a corresponding dicarboxylic acid derivative, such as a dicarboxylic ester having from 1 to 4 carbon atoms in the alcohol radical, carboxylic anhydrides, or carbonyl chlorides. Examples of polyhydric alcohols include sterically hindered glycols preferably having from 2 to 10, more preferably from 2 to 6, carbon atoms, and bearing at least one alkyl radical in the beta position with respect to the hydroxy group, examples including 2,2-dimethyl-1,3-propanediol, 2-methyl-2-propyl-1,3-propanediol, 2,2-diethyl-1,3-propanediol, 2-ethyl-1,3-hexanediol, 2,5-dimethyl-2,5-hexanediol, 2,2,4-trimethyl-1,3-pentanediol, or mixtures with ethylene glycol, diethylene glycol, 1,4-butanediol, 1,5-pentanediol, 1,6-hexanediol, 1,10-decanediol, 1,3-propanediol and dipropylene glycol. Depending on the properties required, the polyhydric alcohols can be used alone or, if appropriate, in a mixture with one another. Other suitable compounds include esters of carbonic acid with the diols mentioned, in particular those having from 3 to 6 carbon atoms, examples including 2,2-dimethyl-1,3-propanediol or 1,6-hexanediol, condensates of hydroxycarboxylic acids, such as hydroxycaproic acid, and polymerization products of lactones, for example of unsubstituted or substituted caprolactones. Polyesterdiols preferably used include neopentyl glycol polyadipates and 1,6-hexanediol neopentyl glycol polyadipates. The polyesterdiols can be used individually or in the form of mixtures with one another.

If appropriate, other polyols can be used alongside polyesterdiols, examples including polycarbonatediols, polyetherdiols, and mixtures of these.

Polycarbonates which have hydroxy groups and which suitably be used include those of the type known per se, by way of example capable of preparation via reaction of diols, such as (1,3)-propanediol, (1,4)-butanediol and/or (1,6)-hexanediol, diethylene glycol, triethylene glycol, tetraethylene glycol or thiodiglycol with diaryl carbonates, e.g. diphenyl carbonate or phosgene (as described in DE-B 16 94 080 and DE-A 22 21 751 both incorporated herein by reference).

Alongside the polyester polyols and the polycarbonatediols, it is also possible to use mixtures comprising a polyether polyol and a polyester polyol and mixtures comprising a polyether polyol and a polycarbonatediol, each with a number-average molar mass of preferably from about 600 to about 5000 g/mol, more preferably from 700 to 4200 g/mol.

Suitable chain extenders C) used may include diols, diamines or amino alcohols whose number average molecular weight is from about 60 to about 500, preferably aliphatic diols having from 2 to 14 carbon atoms, e.g. ethanediol, 1,6-hexanediol, diethylene glycol, dipropylene glycol and in particular 1,4-butanediol. However, other suitable compounds are diesters of terephthalic acid with glycols having from 2 to 4 carbon atoms, e.g. bis(ethylene glycol) terephthalate or bis(1,4-butanediol) terephthalate, hydroxyalkylene ethers of hydroquinone, e.g. 1,4-di(hydroxyethyl)hydroquinone, ethoxylated bisphenols, (cyclo)aliphatic diamines, e.g. isophoronediamine, ethylenediamine, 1,2-propylenediamine, 1,3-propylenediamine, N-methyl-1,3-propylenediamine, 1,6-hexamethylenediamine, 1,4-diaminocyclohexane, 1,3-diaminocyclohexane, N,N'-dimethylethylenediamine and 4,4'-dicyclohexylmethanediamine and aromatic diamines, e.g. 2,4-tolylenediamine and 2,6-tolylenediamine, 3,5-diethyl-2,4-tolylenediamine and 3,5-diethyl-2,6-tolylenediamine and primary mono-, di-, tri- or tetraalkyl-substituted 4,4'-diaminodiphenylmethanes or amino alcohols, such as ethanolamine, 1-aminopropanol, 2-aminopropanol. It is also possible to use mixtures of the abovementioned chain extenders. Alongside these, it is also possible to add relatively small amounts of crosslinking agents of functionality three or greater, for example glycerol, trimethylolpropane, pentaerythritol, sorbitol. It is particularly preferable to use 1,4-butanediol, 1,6-hexanediol, isophoronediamine and mixtures of these.

It is also possible to use if desired for any reason, very small amounts of conventional monofunctional compounds, for example as chain terminators or mold-release agents. By way of example, mention may be made of alcohols, such as octanol and stearyl alcohol, or amines, such as butylamine and stearylamine.

The molar ratios of the structural components can vary over a wide range, thus permitting adjustment of the properties of the product. Molar ratios of polyols to chain extenders of from about 1:1 to about 1:12 have proven successful. The molar ratio of diisocyanates and polyols is preferably from about 1.2:1 to about 30:1. Ratios of from about 2:1 to about 12:1 are particularly preferred. To prepare the TPUs, the amounts of the structural components reacted, if appropriate in the presence of catalysts, of auxiliaries and of additives, can be such that the ratio of equivalents of NCO groups to the total of the NCO-reactive groups, in particular of the hydroxy or amino groups of the lower-molecular-weight diols/triols, and amines and of the polyols may suitably be from about 0.9:1 to about 1.2:1, preferably from about 0.98:1 to about 1.05:1, particularly preferably from about 1.005:1 to about 1.01:1.

The polyurethanes that can be used according to the invention can be prepared without catalysts if desired for any reason; in some cases, however, it can be advisable to use catalysts. The amounts used of the catalysts are generally up to about 100 ppm, based on the total amount of starting materials. Suitable catalysts according to the invention include conventional tertiary amines known from the prior art, e.g. triethylamine, dimethylcyclohexylamine, N-methylmorpholine, N,N'-dimethylpiperazine, 2-(dimethylaminoethoxy)ethanol, diazabicyclo[2.2.2]octane and the like, and also in particular organometallic compounds, such as titanic esters, iron compounds, tin compounds, e.g. stannous diacetate, stannous dioctoate, stannous dilaurate or the dialkyltin salts of aliphatic carboxylic acids. Dibutyltin diacetate and dibutyltin dilaurate are preferred. Amounts of from about 1 to about 10 ppm of these are sufficient to catalyse the reaction.

Alongside the TPU components and the catalysts, it is also possible to add other auxiliaries and additives if desired. By way of example, mention may be made of lubricants, such as fatty acid esters, metal soaps of these, fatty acid amides and silicone compounds, antiblocking agents, inhibitors, stabilizers with respect to hydrolysis, light, heat and discoloration, flame retardants, dyes, pigments, inorganic or organic fillers and/or reinforcing agents or other additives. Reinforcing agents include in particular fibrous reinforcing agents, such as inorganic fibers, which can be produced according to methods known in the prior art. The fibers can also have been sized if desired. Further details concerning the auxiliaries and additives mentioned can be found in the technical literature, for example J. H. Saunders, K. C. Frisch: "High Polymers", Volume XVI, Polyurethane [Polyurethanes], Part 1 and 2, Interscience Publishers 1962 and 1964, R. Gächter, H. Müller (Ed.): Taschenbuch der Kunststoff-Additive [Plastics additives], 3rd Edition, Hanser Verlag, Munich 1989, or DE-A 29 01 774 all incorporated herein by reference.

The thermoplastically processible polyurethane elastomers can preferably be constructed by what is known as the prepolymer process known in the art. In the prepolymer process, an isocyanate-containing prepolymer is formed from the polyol and from the diisocyanate, which is then reacted with a chain extender. The TPUs can be prepared continuously and/or batchwise. Well known industrial preparation processes for making TPU's include the belt process and the extruder process.

The median particle diameter $d_{50}$ of the plastics powder is typically from about 50 to about 800 μm, preferably from about 100 to about 500 μm.

In order to set the desired median particle diameter, the plastic can be, for example, ground. Various known mills can be used for this purpose, including for example, a fine-product impact mill, a spiral jet mill, a counter-current fluidized-bed mill, a vibratory mill to name a few. In the case of soft, ductile plastics, the grinding process can take place at temperatures below room temperature if desired.

For the present inventive process, the active ingredient powder is preferably mixed with the plastics powder to give a powder mixture.

The resultant powder mixture is advantageously run into the aperture of an extruder by way of suitable metering equipment, such as by a K-Tron & Soder screw, or by a differential weigh feeder. As a function of temperature profile and mixing ratio, the mixing ratio can be varied widely. By way of example, it is possible to use powder mixtures whose ratio by weight of plastics powder to active ingredient powder is from about 95:1 to about 5:95, preferably from about 90:10 to about 10:95.

If desired, further plastic can be extruded in addition to the powder mixture. The further plastic is preferably the same as that used for preparation of the powder mixture but it can also be different. A masterbatch comprising active ingredient can also be directly melted with the plastic, or can be mixed with the previously prepared plastics melt if desired for any reason.

Known techniques such as kneader or screw machines can be used for the mixing/homogenization of the active ingredient/polymer powder mixture with the polymer, preferably in single- or twin-screw extruders in the temperature range from about 150 to about 200° C. The mixing of the components during the extrusion process preferably achieves a substantially homogeneous dispersion at the molecular level of the active ingredient within the polymer matrix, without any need for additional operation.

The active ingredient concentration of the resultant plastics composition can preferably be from about 0.1 to about 5% by weight. The plastics composition is suitable for example, for use for production of catheters and of other medical-technology products and/or in any application where an antimicrobial property may be beneficial. The plastics composition of the present invention and its method of manufacture may also be advantageous for uses where a bis(4-(substituted amino)-1-pyridinium) alkane ingredient provides a benefit.

The examples below are intended to illustrate the invention but not to restrict it.

EXAMPLES

Example 1 (Comparative Example)

Commercially available aromatic polyetherurethane with 20% by weight of barium sulphate: TECOTHANE TT 2085 A-B20 of Shore hardness 85 A (NOVEON, Woburn Mass.) in the form of commercially available lenticular pellets of dimensions about 2 mm was extruded in a ZSK twin-screw extruder to give cylindrical pellets comprising no active ingredient. The active ingredient ciprofloxacin hydrochloride ($d_{50}$=9.13 μm) was metered in the form of pure powder into barrel section 1 of the BRABENDER twin-screw extruder by means of a twin-screw differential weigh feeder. This gave a melt which, after cooling in a water/air bath and strand pelletization gave colourless, slightly cloudy cylindrical pellets with 1% by weight of ciprofloxacin hydrochloride.

To determine the release profile of the active ingredient incorporated, extrudate specimens (diameter 2 mm and length about 17 cm) were taken and the pellets were injection-moulded to give test specimens (sheets).

To study the distribution of the active ingredient in the polymer, scanning electron (SEM)micrographs were prepared (FIG. 1) of the surface of a cylindrical pellet. The inhomogeneous distribution of the active ingredient particles in the matrix is clear.

Example 2

Commercially available lenticular pellets of TECOTHANE TT2085A-B20 whose size was about 2 mm were milled at −40° C. to give a powder, which was then sieved to give two fractions. A first fraction with $d_{50}$=300 μm was used for the inventive examples, and a second fraction >500 μm was not used.

10 g of ciprofloxacin hydrochloride ($d_{50}$=9.13 μm) were mixed in an intensive mixer with 990 g of TECOTHANE TT2085A-B20 powder ($d_{50}$=300 μm) comprising no active ingredient. The polymer/active ingredient powder mixture was metered into barrel section 1 of the extruder. The cylindrical pellets comprising active ingredient were extruded in a BRABENDER ZSK twin-screw extruder. A clear melt was obtained and after cooling in a water/air bath and strand pelletization gave colorless, clear cylindrical pellets with 1% by weight of ciprofloxacin hydrochloride.

To determine the release profile of the active ingredient incorporated, extrudate specimens (diameter 2 mm and length about 17 cm) were taken and the pellets were injection-molded to give test specimens (sheets).

Figure 2:
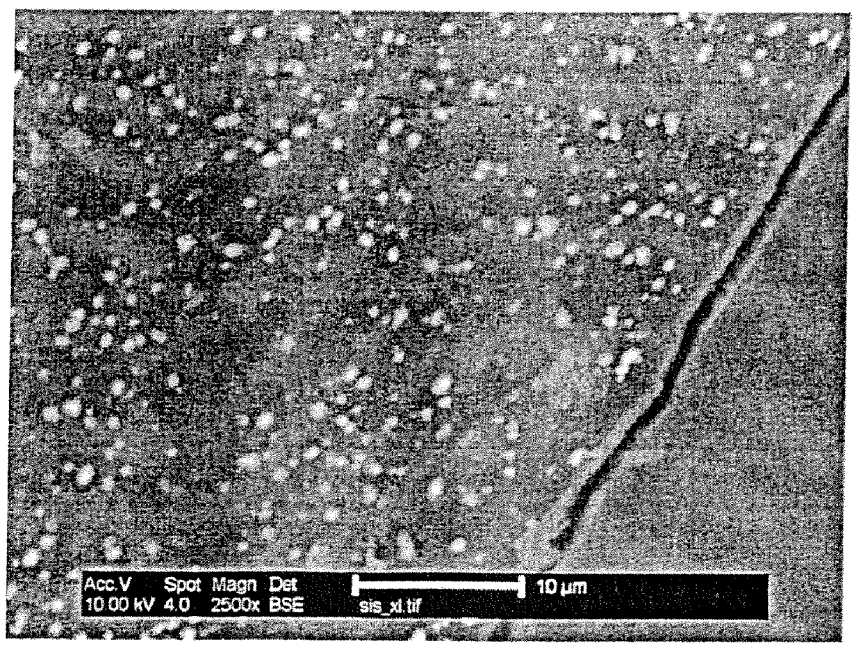
FIG. 2 is an SEM micrograph of a composition according to the present invention.

To study the distribution of the active ingredient in the polymer, scanning electron (SEM) micrographs were prepared (FIG. 2) of the surface of a cylindrical pellet. The homogeneous distribution of the active ingredient particles in the matrix is clear.

Example 3

10 g of octenidine dihydrochloride powder ($d_{50}$=13.4 µm) were mixed in an intensive mixer with 990 g of TECOTHANE TT2085A-B20 powder ($d_{50}$=300 µm) comprising no active ingredient. The cylindrical pellets comprising active ingredient were extruded in a ZSK twin-screw extruder. A clear melt was obtained and after cooling in a water/air bath and strand pelletization gave colourless, clear cylindrical pellets with 1% by weight of octenidine dihydrochloride.

For elution experiments to determine the release profile of the active ingredient incorporated, extrudate specimens (diameter 2 mm and length about 17 cm) were taken and the pellets were injection-molded to give test specimens (sheets).

The elution experiments were carried out on injection-molded sheets which had been cut into pieces of size 1 cm². Each of the specimens weighed about 2.2 g and had surface area of 20.5 cm². 16 ml of demineralized water was used as eluent. After each of 1 h, 4 h, 8 h, 24 h, 48 h, 120 h and 360 hours (15 days), the aqueous eluent was replaced by fresh eluent and the active ingredient content in the solutions was determined.

TABLE 1

Eluted amount of active ingredient, based on the amount initially present

| Hours | Example 1 (non-inventive) | Example 2 | Example 3 |
|---|---|---|---|
| 1.00 | 0.111% | 0.096% | 0.116% |
| 4.00 | 0.125% | 0.125% | 0.225% |
| 8.00 | 0.133% | 0.162% | 0.302% |
| 24.00 | 0.147% | 0.214% | 0.524% |
| 48.00 | 0.221% | 0.265% | 0.785% |
| 120.00 | 0.236% | 0.390% | 1.502% |
| 360.00 | 0.302% | 0.714% | 3.295% |

Taking a total across all 7 of the solutions, the amount extracted of the initial amount of active ingredient after 15 days was 0.302% from the sheets of comparative Example 1, 0.714% from those of Example 2 and 3.295% from the sheets of Example 3. After as little as 48 hours, there is very little continued diffusion of active ingredient from the bulk to the surface in the case of comparative Example 1. Agglomeration of the active ingredient particles has—as shown by the scanning electromicrograph—formed "active ingredient nests", and there is major inhibition of active ingredient transport from these to the interface with the solvent.

Additional advantages, features and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

As used herein and in the following claims, articles such as "the", "a" and "an" can connote the singular or plural.

In the present description and in the following claims, to the extent a numerical value is enumerated, such value is intended to refer to the exact value and values close to that value that would amount to an insubstantial change from the listed value.

All documents and standards referred to herein are expressly incorporated herein by reference in their entireties

What is Claimed is:

1. A process for preparing a composition comprising a thermoplastic polyurethane or thermoplastic elastomer and an active ingredient comprising at least one bis(4-(substituted amino)-1-pyridinium)alkane, said process comprising
preparing a powder mixture by mixing an active ingredient powder with a thermoplastic polyurethane or thermoplastic elastomer powder having a median particle diameter $d_{50}$ from about 50 to about 800 µm, and
extruding the powder mixture, optionally with further plastic.

2. The process according to claim 1, wherein the ratio by weight of the thermoplastic polyurethane or thermoplastic elastomer powder to active ingredient powder is from about 95:1 to about 5:95.

3. The process according to claim 1, wherein the active ingredient concentration of the resultant composition is from 0.1 to 5% by weight.

4. The process according to claim 1, wherein the median particle size $d_{50}$ of the active ingredient powder is from about 0.5 to about 20 µm.

5. The process according to claim 1, wherein the thermoplastic polyurethane or thermoplastic elastomer is a thermoplastic elastomer.

6. The process according to claim 5, wherein the thermoplastic elastomer is a copolyester or a polyether block amide.

7. The process according to claim 1, wherein the active ingredient is selected from the group consisting of substances of formulae (I) and (II)
wherein

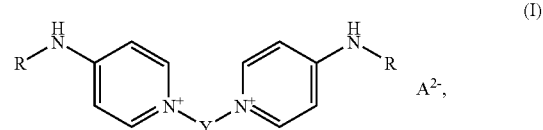

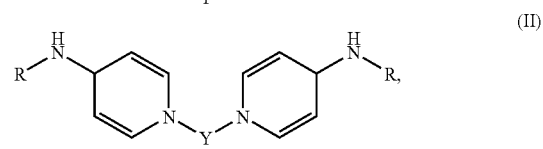

Y is independently an alkylene group having from 4 to 18 carbon atoms,
R is independently $C_6$-$C_{18}$-alkyl, $C_5$-$C_7$-cycloalkyl or halogen-atom-substituted phenyl, and
A is independently two monovalent anions or one divalent anion.

8. The process according to claim 1, wherein the thermoplastic polyurethane or thermoplastic elastomer is a thermoplastic polyurethane and the active ingredient comprises octenidine dihydrochloride.

9. A molding comprising a plastics composition obtained according to the process of claim 1.

10. A method for production of a catheter and/or of another medical-technology product comprising forming the molding of claim 9 into said catheter and/or said product.

11. A composition comprising a thermoplastic polyurethane or thermoplastic elastomer and an active ingredient comprising at least one bis(4-(substituted amino)-1-pyridinium) alkane, wherein said thermoplastic polyurethane or thermoplastic elastomer is prepared by a process comprising preparing a powder mixture by mixing an active ingredient powder with the thermoplastic polyurethane or thermoplastic elastomer powder having a median particle diameter $d_{50}$ from about 50 to about 800 μm, and extruding the powder mixture, optionally with further plastic, wherein, said active ingredient being present in fine dispersion in said composition such that said active ingredient in capable of being released from said composition over at least 15 days, with the proviso said active ingredient was not metered into a melt of said thermoplastic polyurethane or thermoplastic elastomer.

12. The composition of claim 11, wherein said composition is formed by mixing of a powder of said thermoplastic polyurethane or thermoplastic elastomer with a powder of said active ingredient.

13. The composition of claim 12, wherein the ratio by weight of the thermoplastic polyurethane or thermoplastic elastomer powder to active ingredient powder is from about 95:1 to about 5:95.

14. The composition of claim 12, wherein the active ingredient concentration of the resultant composition is from 0.1 to 5% by weight.

15. The composition of claim 12, wherein the median particle size $d_{50}$ of the active ingredient powder is from about 0.5 to about 20 μm.

16. The composition of claim 12, wherein the thermoplastic polyurethane or thermoplastic elastomer is a thermoplastic elastomer.

17. The composition of claim 16, wherein the thermoplastic elastomer is a copolyester or a polyether block amide.

18. The composition of claim 12, wherein the active ingredient is selected from the group consisting of substances of formulae (I) and (II) wherein

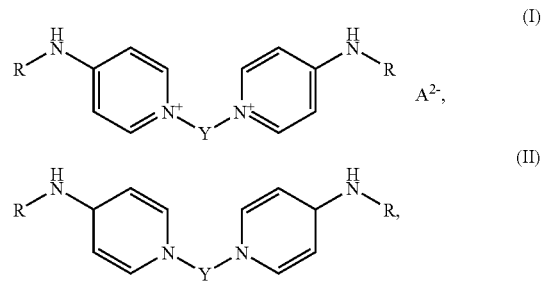

Y is independently an alkylene group having from 4 to 18 carbon atoms,

R is independently $C_6$-$C_{18}$-alkyl, $C_5$-$C_7$-cycloalkyl or halogen-atom-substituted phenyl, and A is independently two monovalent anions or one divalent anion.

19. The composition of claim 12, wherein the thermoplastic polyurethane or thermoplastic elastomer is a thermoplastic polyurethane and the active ingredient comprises octenidine dihydrochloride.

20. A catheter comprising the composition of claim 11.

21. A catheter comprising the composition of claim 12.

22. A medical product comprising the composition of claim 11.

23. A medical product comprising the composition of claim 12.

24. A catheter comprising the molding of claim 9.

25. A medical product comprising the molding of claim 9.

* * * * *